Figure 1:
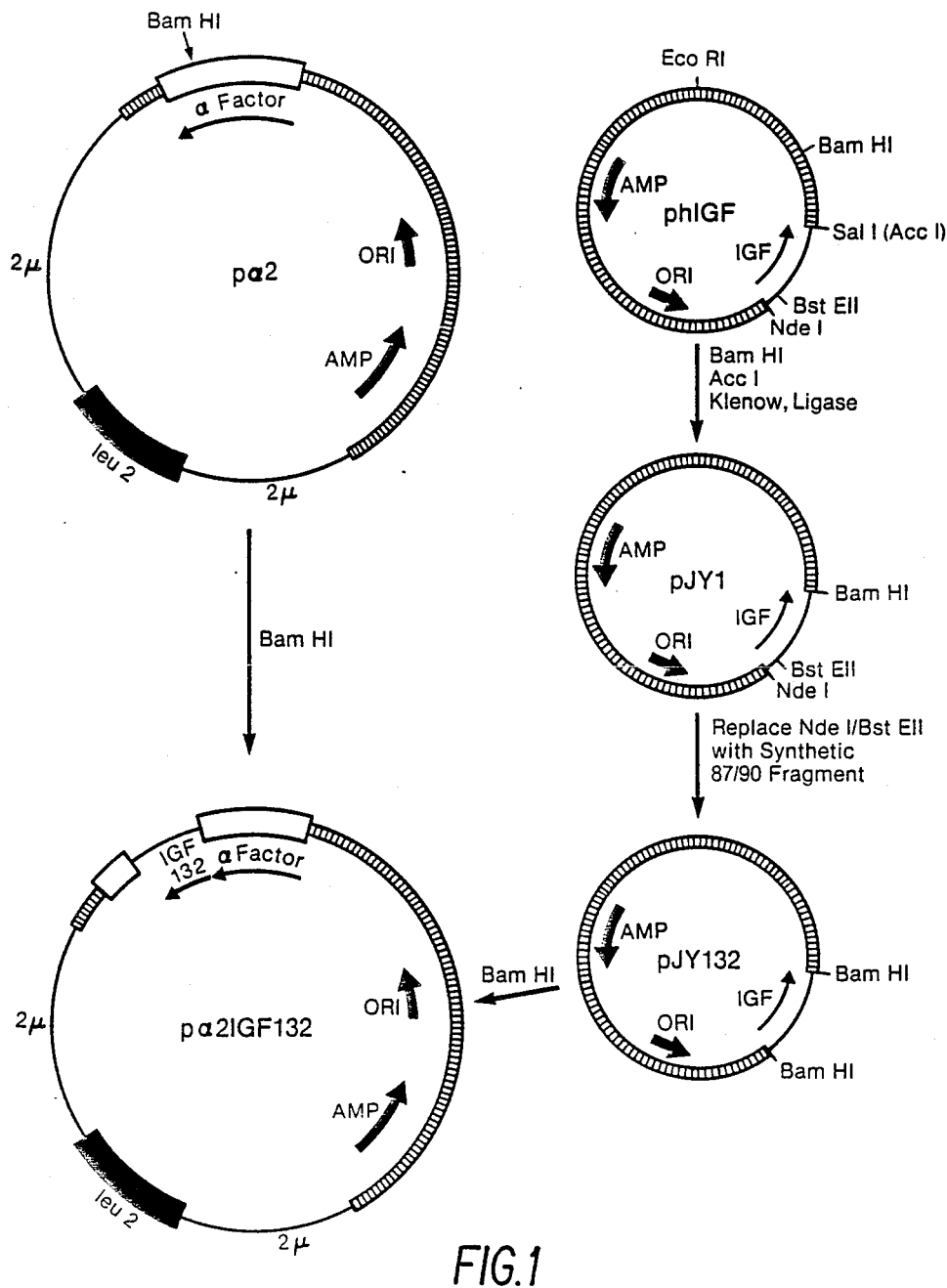

United States Patent [19]

Applebaum et al.

[11] Patent Number: 4,876,242

[45] Date of Patent: Oct. 24, 1989

[54] HUMAN INSULIN-LIKE GROWTH FACTOR ANALOGES WITH REDUCED BINDING TO SERUM CARRIER PROTEINS AND THEIR PRODUCTION IN YEAST

[75] Inventors: Joy D. Applebaum, North Brunswick; Marvin L. Bayne, Westfield; Margaret A. Cascieri, East Windsor, all of N.J.

[73] Assignee: Merck & Co., Inc., Rahway, N.J.

[21] Appl. No.: 99,367

[22] Filed: Sep. 21, 1987

[51] Int. Cl.$^4$ .................. A61K 37/26; C07K 7/10; C07K 7/40

[52] U.S. Cl. .................................. 514/3; 514/12; 514/4; 530/303; 530/324; 435/172.3

[58] Field of Search .................. 530/303, 324, 345; 514/3, 4, 12; 435/172.3

[56] References Cited

FOREIGN PATENT DOCUMENTS

WO 87/01038 2/1987 PCT Int'l Appl. .

OTHER PUBLICATIONS

Bayne et al., Chem. Abstr., vol. 109, No. 17150r, (1988).
Cascieri et al., Endocrinology, vol. 123, No. 1, pp. 373–381, (1988).
Bayne et al., Journal of Biological Chemistry 263, pp. 6233–6239, (1988).
Joshi et al., (I) Biochemistry 24, 4208–4242, (1985).
DeVroede et al., *Proc. Nat. Acad Sci. USA*, 82, 3010–3014, (1985).
Joshi et al., (II) *Biochem and Biophys Res. Comm.* 133, 423–429, (1985).
Blundell et al., (I) *Proc. Nat. Acad. Sci. USA* 75 180–184, (1978).
Blundell et al. (II) *Fed. Proc. Am. Soc. Exp. Biol.* 42, 2592–2597, (1983).
Li et al., *Proc. Nat. Acad. Sci.* USA 80, 2216–2220, (1983).

*Primary Examiner*—Delbert R. Phillips
*Assistant Examiner*—Christina Chan
*Attorney, Agent, or Firm*—David L. Rose; Hesna J. Pfeiffer

[57] ABSTRACT

A synthetic gene encoding a 71-amino acid analog of human insulin-like grouwth factor (hIGF-I) has been constructed and expressed in the yeast, *Saccharomyces cerevisiae*. The protein analog, IGF132, contains the first 17 amino acids of the B chain of human insulin in place of the first 16 amino acids of hIGF-I. The purified hybrid protein has high affinity for the type I IGF receptor (12 nM) yet has drastically reduced affinity for human serum carrier proteins (>1000 nM). This analog is 5 to 10 times more active than normal hIGF-I in stimulating DNA synthesis in 3T3 cells and is a more active growth factor in vivo due to its reduced affinity for serum carrier proteins. Other proteins with similar properties have also been constructed. The protein analogs thus have a variety of utilities such as in promoting lactation in animals; promoting growth and feed efficiency in animals; improving carcass quality by increasing lean and decreasing fat; promoting wound healing in animals, including humans; promoting glucose utilization in skeletal muscle, and stimulating erythropoiesis, the production of red blood cells.

13 Claims, 13 Drawing Sheets

Nde I

```
            Ile Leu Ser Leu Asp Lys Arg Phe Val Asn Gln His
TATGCCGG ATC CTT TCC TTG GAT AAA AGA TTT GTA AAC CAA CAT
  ACGGCC TAG GAA AGG AAC CTA TTT TCT AAA CAT TTG GTT GTA AAC ACA
```

BstE II

```
Leu Cys Gly Ser His Leu Val Glu Ala Leu Tyr Leu Val Cys
TTG TGT GGC TCC CAT CTG GTT GAA GCT TTG TAC TTG GTT TGC G
    CCG AGG GTA GAC CAA CTT CGA AAC ATG AAC CAA ACG C CACTG
```

*FIG.2*

IGF-132

```
                                                           ATC CTT TCC TTG GAT AAA AGA
                                                           TAG GAA AGG AAC CTA TTT TCT

Phe Val Asn Gln His Leu Cys Gly Ser His Leu Val Glu Ala Leu Tyr Leu Val Cys
TTT GTA AAC CAA CAT TTG TGT GGC TCC CAT CTC GTT GAA GCT TTG TAC TTG GTT TGC
AAA CAT TTG GTT GTA AAC ACA CCG AGG GTA GAG CAA CTT CGA AAC ATG AAC CAA ACG

Gly Asp Arg Gly Phe Tyr Phe Asn Lys Pro Thr Gly Tyr Gly Ser Ser Arg Arg
GGT GAC CGC GGT TTC TAC TTC AAC AAA CCG ACT GGT TAC GGT TCT TCT AGA CGT
CCA CTG GCG CCA AAG ATG AAG TTG TTT GGC TGA CCA ATG CCA AGA AGA TCT GCA

Ala Pro Gln Thr Gly Ile Val Asp Glu Cys Cys Phe Arg Ser Cys Asp Leu Arg Arg
GCT CCG CAG ACT GGT ATC GTT GAT GAA TGC TGC TTC AGA TCT TGT GAC CTG CGT CGT
CGA GGC GTC TGA CCA TAG CAA CTA CTT ACG ACG AAG TCT AGA ACA CTG GAC GCA GCA

Leu Glu Met Tyr Cys Ala Pro Leu Lys Pro Ala Lys Ser Ala  *   *
CTC GAG ATG TAC TGC GCA CCG CTG AAA CCG GCT AAA TCT GCT TGA TAA GTCG
GAG CTC TAC ATG ACG CGT GGC GAC TTT GGC CGA TTT AGA CGA ACT ATT CAGCC TAG
```

FIG. 3A

IGF-122

```
                         Gly Pro Glu Thr Leu Cys Gly Ala Glu Leu Val Asp Ala Leu Tyr Leu Val Cys
ATC CTT TCC TTG GAT AAA AGA GGT CCG GAA ACT TTG TGT GGT GCT GAG CTC GTT GAC GCT CTG TAC CTC GTT TGC
TAG GAA AGG AAC CTA TTT TCT CCA GGC CTT TGA AAC ACA CGA CCA CTC GAG CAA CTG CGA GAC ATG GAG CAA ACG

Gly Asp Arg Gly Phe Tyr Phe Asn Lys Pro Thr Gly Tyr Gly Ser Ser Ser Arg Arg
GGT GAC CGC GGT TTC TAC TTC AAC AAA CCG ACT GGT TAC GGT TCT TCT TCT AGA.CGT
CCA CTG GCG CCA AAG ATG AAG TTG TTT GGC TGA CCA ATG CCA AGA AGA AGA TCT GCA

Ala Pro Gln Thr Gly Ile Val Asp Glu Cys Cys Phe Arg Ser Cys Asp Leu Arg Arg
GCT CCG CAG ACT GGT ATC GTT GAT GAA TGC TGC TTC AGA TCT TGT GAC CTG CGT CGT
CGA GGC GTC TGA CCA TAG CAA CTA CTT ACG ACG AAG TCT AGA ACA CTG GAC GCA GCA

Leu Gly Met Tyr Cys Ala Pro Leu Lys Pro Ala Lys Ser Ala  *   *
CTC GAG ATG TAC TGC GCA CCG CTG AAA CCG GCT AAA TCT GCT TGA TAA GTCG
GAG CTC TAC ATG ACG CGT GGC GAC TTT GGC CGA TTT AGA CGA ACT ATT CAGCCTAG
```

FIG.3B

IGF-130

```
                Gly Pro Gln Ala Leu Cys Gly Ala Glu Leu Val Asp Ala Leu Gln Phe Val Cys
ATC CTT TCC TTG GAT AAA AGA GGT CCG CAA GCT TTG TGT GGT GCT GAG CTC GTT GAC GCT CTG CAG TTC GTT TGC
TAG GAA AGG AAC CTA TTT TCT CCA GGC GTT CGA AAC ACA CCA CGA CTC GAG CAA CTG CGA GAC GTC AAG CAA ACG

Gly Asp Arg Gly Phe Tyr Phe Asn Lys Pro Thr Gly Tyr Gly Ser Ser Ser Arg Arg
GGT GAC CGC GGT TTC TAC TTC AAC AAA CCG ACT GGT TAC GGT TCT TCT TCT AGA CGT
CCA CTG GCG CCA AAG ATG AAG TTG TTT GGC TGA CCA ATG CCA AGA AGA AGA TCT GCA

Ala Pro Gln Thr Gly Ile Val Asp Glu Cys Cys Phe Arg Ser Cys Asp Leu Arg Arg
GCT CCG CAG ACT GGT ATC GTT GAT GAA TGC TGC TTC AGA TCT TGT GAC CTG CGT CGT
CGA GGC GTC TGA CCA TAG CAA CTA CTT ACG ACG AAG TCT AGA ACA CTG GAC GCA GCA

Leu Glu Met Tyr Cys Ala Pro Leu Lys Pro Ala Lys Ser Ala  *    *
CTC GAG ATG TAC TGC GCA CCG CTG AAA CCG GCT AAA TCT GCT TGA TAA GTCG
GAG CTC TAC ATG ACG CGT GGC GAC TTT GGC CGA TTT AGA CGA ACT ATT CAGCCTAG
```

FIG. 3C

IGF-252

```
                                    Gly Pro Gln Ala Leu Cys Gly Ala Glu Leu Val Asp Ala Leu Tyr Leu Val Cys
ATC CTT TCC TTG GAT AAA AGA TTT TCT CCA GGC GTT CGA AAC ACA CCA CGA CTT GGT GCT GAG CTC GTT GAC GCT CTG TAC CTC GTT TGC
TAG GAA AGG AAC CTA TTT TCT AAG AGG TAG TTG TGT GGT GCT TGA CCA CGA CTC GAG CAA CTG CGA GAC ATG GAG CAA ACG

Gly Asp Arg Gly Phe Tyr Phe Asn Lys Pro Thr Gly Tyr Gly Ser Ser Ser Arg Arg
GGT GAC CGC GGT TTC TAC TTC AAC AAA CCG ACT GGT TAC GGT TCT TCT TCT AGA CGT
CCA CTG GCG CCA AAG ATG AAG TTG TTT GGC TGA CCA ATG CCA AGA AGA AGA TCT GCA

Ala Pro Gln Thr Gly Ile Val Asp Glu Cys Cys Phe Arg Ser Cys Asp Leu Arg Arg
GCT CCG CAG ACT GGT ATC GTT GAT GAA TGC TGC TTC AGA TCT TGT GAC CTG CGT CGT
CGA GGC GTC TGA CCA TAG CAA CTA CTT ACG ACG AAG TCT AGA ACA CTG GAC GCA GCA

Leu Glu Met Tyr Cys Ala Pro Leu Lys Pro Ala Lys Ser Ala *       *
CTC GAG ATG TAC TGC GCA CCG CTG AAA CCG GCT AAA TCT GCT TGA TAA GTCG
GAG CTC TAC ATG ACG CGT GGC GAC TTT GGC CGA TTT AGA CGA ACT ATT CAGCCTAG
```

FIG. 3D

HPLC Purification of B-Chain Mutant (A), [Tyr 15, Leu 16] IGF I (B), [Gln 3, Ala 4] IGF I (C) and [Gln 3, Ala 4, Tyr 15, Leu 16] IGF I (D)

HUMAN INSULIN-LIKE GROWTH FACTOR ANALOGES WITH REDUCED BINDING TO SERUM CARRIER PROTEINS AND THEIR PRODUCTION IN YEAST

BACKGROUND OF THE INVENTION

The incorporation of fragments of the insulin molecule into IGF-I has previously been attempted in the form of two-chain disulfide-linked insulin-like structures. These molecules have considerably reduced biological activity relative to IGF-I and serum carrier protein binding is still significant rendering the in vitro activity of such compounds of little in vivo utility. See Joshi et al. *Biochemistry* 24: 4208–42 (1985); DeVroede et al. *Proc. Nat. Acad. Sci.* U.S.A. 82: 3010–14 (1985); and Joshi et al. *Biochem. and Biophys. Res. Comm.* 133: 423–429 (1985). The IGF-I analogs described in this invention are produced as single chain IGF-I-like molecules with equal potency to IGF-I at the type I IGF receptor and very little serum protein binding rendering such analogs of significant potential in vivo utility.

SUMMARY OF THE INVENTION

Human insulin-like growth factor I (hIGF-I, also called somatomedin C) is a 70-amino acid protein purified from human serum. It is believed to mediate many of the effects of growth hormone; in particular it has been demonstrated to stimulate growth in hypophysectomized rats. In addition, IGF-I has been shown to promote cell growth and differentiation of various cell types.

Human IGF-I shows a remarkable amino acid sequence homology to insulin. This homology is the basis of a computer generated three-dimensional structural model for hIGF-I. (Blundell et al. *Proc. Natl. Acad. Sci. U.S.A.* 75: 180–184 (1978) and Blundell et al. *Fed. Proc. Am. Soc. Exp. Biol.* 42: 2592–2597 (1983)). This model predicts that a portion of the insulin receptor binding region is conserved within the IGF-I molecule explaining the ability of hIGF-I to bind to insulin receptors. The model also suggests regions of hIGF-I molecule which may be responsible for binding to serum carrier proteins.

One of the major differences between hIGF-I and insulin is that in normal human blood, greater than 99% of the IGF-I is bound to serum carrier proteins which do not readily cross the capillary barrier. Thus most of the IGF in serum is inactive. The physiological significance of the IGF carrier protein complex is not clear. The presence of serum binding proteins is a barrier to the bioactivity and bioavailability of exogenously administered IGF-I.

Investigations into the role of serum binding proteins in the bioactivity of IGF-I could lead potentially to important bioactive compounds. Our approach was to create a IGF-I analog that retains efficient binding to the type I receptor, yet would have reduced binding to serum carrier proteins. The design of this analog is based on the observation that insulin does not bind to serum carrier proteins. Evidence from synthetic, insulin-like two chain analogs suggests that amino acids of IGF-I responsible for carrier protein binding are in the B region of IGF-I. Therefore a synthetic gene for human IGF-I was modified to encode an IGF-I analog in which the first 16 amino acids of hIGF-I are replaced by the first 17 amino acids of the B chain of human insulin. The synthetic gene is then placed in a yeast recombinant DNA expression system and the peptide analog which is produced by the modified yeast cells is extracted therefrom and purified. Additional modifications of the IGF-I molecule have been carried out leading to additional analogs, all of which have substantial IGF-I type I receptor binding and reduced binding to serum carrier proteins.

Thus, it is an object of this invention to describe the preparation of synthetic genes encoding for IGF-I analogs and to describe the incorporation of such genes in a microorganism. A further object is to describe the preparation of the IGF-I analogs from culturing the genetically modified microorganism. A still further object of this invention is to describe the properties and uses of the IGF-I analogs thus prepared. Still further objects will become apparent from reading the following description.

DESCRIPTION OF THE INVENTION

Figure 6:
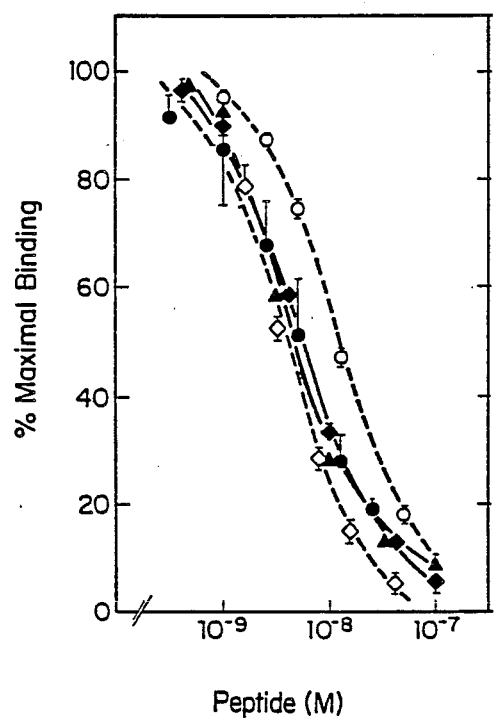
Figure 7:
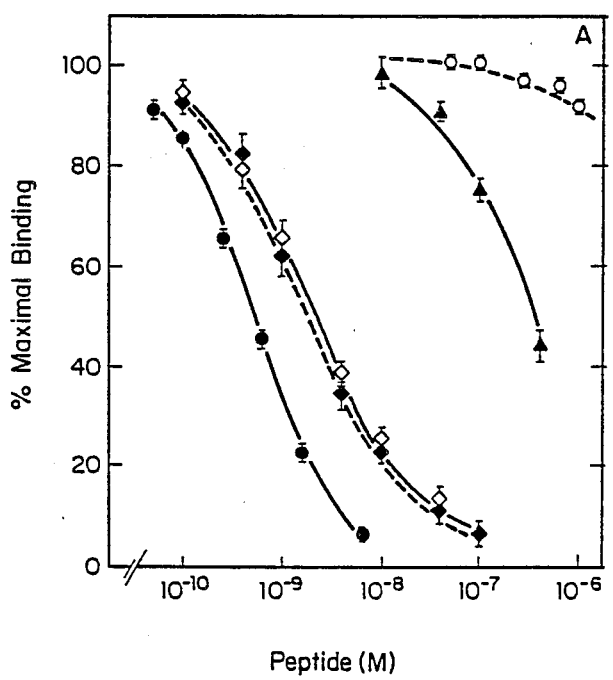
Figure 8:
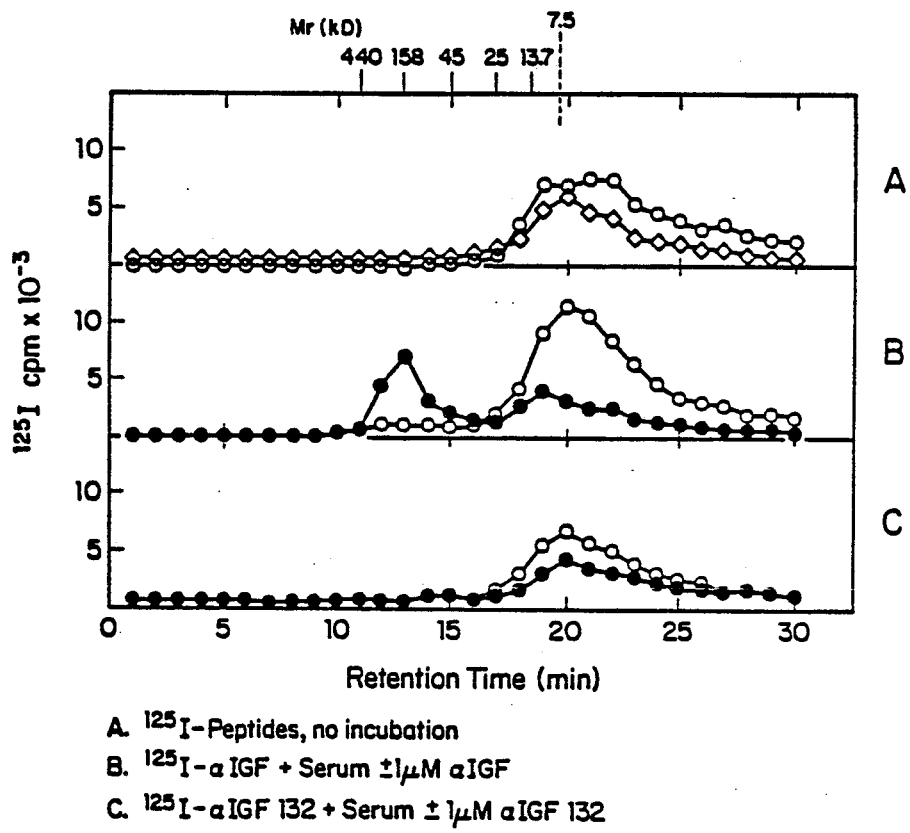
Figure 9:
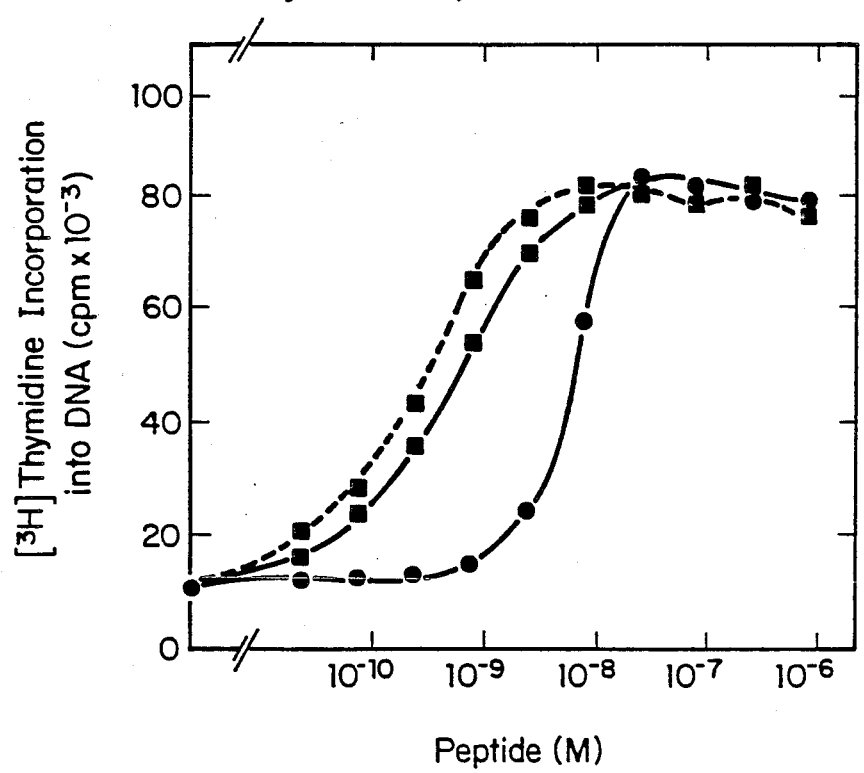

We have expressed a synthetic gene encoding a 71-amino acid analog of human IGF-I. This analog IGF132, contains the first 17 amino acids of human insulin B chain in place of the first 16 amino acids of hIGF-I. The analog has near equal affinity for the type I IGF receptor as compared to normal human IGF-I (FIG. 6). Analog IGF132, however, has greatly reduced binding to both human and rat serum carrier proteins (FIGS. 7 and 8). Thus, this new protein retains nearly full activity at the type I IGF receptor but does not bind to serum components. It is expected that this analog will be more potent in vivo than normal IGF-I. This analog is 10 times more potent than normal IGF-I in stimulating DNA synthesis in 3T3 cells (FIG. 9).

The synthetic genes of this invention encode for a peptide which is an analog of human insulinlike growth factor (hIGF-I) and has the following structure where the letter designation for the constituent amino acids have the definitions given below:

$$A_1\text{-}A_2\text{-}A_3\text{-}A_4\text{-LCG-}A_5\text{-}A_6\text{-LV-}A_7\text{-AL-}A_8\text{-}A_9\text{-}R_1$$

wherein:
$A_1$ is G, V, or FV;
$A_2$ is P or N;
$A_3$ is E or Q;
$A_4$ is T, H or A;
$A_5$ is A or S;
$A_6$ is E or H;
$A_7$ is D or E;
$A_8$ is Q or Y;
$A_9$ is F or L; and
$R_1$ is the remainder of the hIGF-I peptide consisting of 54 amino acids as follows: VCGDRGFYFNKPTGYGSSSRRAPQTGIVDECCFRSCDLRRLEMYCAPLKPAKSA with the exception that the following gene: GPETLCGAELVDALQF-$R_1$ which is the wild type hIGF-I and is excluded from the foregoing definition.

While the amino acid letter designations are generally well known to those skilled in the art, for purposes of clarity, the definitions as used herein are as follows:
A—Alanine
C—Cysteine
D—Aspartic acid
E—Glutamic acid
F—Phenylalanine G—Glycine
H—Histidine
I—Isoleucine
K—Lysine
L—Leucine
M—Methionine
N—Asparagine
P—Proline
Q—Glutamine
R—Arginine
S—Serine
T—Threonine
V—Valine
Y—Tyrosine Preferred variations of the foregoing peptide analogs are as follows:

$A_1$ is G, V or FV;
$A_2$ is P or N;
$A_3$ is Q;
$A_4$ is A;
$A_5$ is A or S;
$A_6$ is E or H;
$A_7$ is D or E;
$A_8$ is Y; and
$A_9$ is L.

Additionally, specific examples of such compounds are as follows:

FVNQHLCGSHLVEALYL-$R_1$ (Compound A or IGF132)
GPETLCGAELVDALYL-$R_1$ (Compound B or IGF122)
GPQALCGAELVDALQF-$R_1$ (Compound C or IGF130)
GPQALCGAELVDALYL-$R_1$ (Compound D or IGF252)
VNQHLCGSHLVGALYL-$R_1$ The peptide analogs can be produced by procedures similar to methods existing for the preparation of natural hIGF-I peptide, and modifications thereof which would be well-known to those skilled in the art. Specifically, these analogs may be synthesized chemically using procedures developed for human IGF-I. See for example Li et al. *Proc. Natl. Acad. Sci. U.S.A.* 80: 2216–2220 (1983). In accordance with the present invention the IGF-I analogs may also be produced following the transformation of susceptible bacterial, yeast or tissue culture cell hosts with recombinant plasmids that include DNA sequences capable of directing the expression of IGF-I analogs. The DNA sequence may be prepared synthetically, chromosomally, by recombinant DNA techniques or combination thereof. DNA sequences capable of directing the expression of IGF-I analogs could also be introduced into the germ line of animals or extra chromasomally to produce transgenic animals endogenously producing the IGF-I analogs.

The synthetic genes of this invention are prepared using recombinant DNA biotechnology techniques well known to those skilled in the art. FIG. 1 outlines the steps in combining the plasmids pα2 and phIGF with the inclusion of the synthetic gene of this invention.

The instant synthetic gene produces analogs of hIGF-I which have substantial activity but, because they are not apparently bound to serum proteins have levels of activity which, when taken on a molar or weight basis are considerably more active than wild-type hIGF-I. The compounds are thus highly active as agents to increase the yield and efficency of milk production of animals, particularly ruminant animals such as cows. The compounds are also useful as growth promotant agents in food producing animals by increasing the rate of gain, feed efficency and carcass quality. The compounds are further useful as agents to promote wound healing and to stimulate erythropoiesis (the manufacture of red blood cells).

When used to increase milk production or as an animal growth promotant the compounds are administered parenterally such as by subcutaneous, intramuscular or intravenous injection or by a sustained release subcutaneous implant. In subcutaneous, intramuscular and intravenous injection the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic prparation using solketal, glycerol, formal and aqueous parenteral formulations are also used. The active compound or compounds are dissolved or suspended in the parenteral formulation for administration; such formulations generally contain from 0.005 to 5% by weight of the active compound.

The instant compounds are effective by significantly increasing the level of milk production or the rate of weight gain or feed efficiency when administered at levels of from 0.1 to 100 mg per kg of animal body weight, preferably at from 1 to 10 mg/kg. When the compounds are administered in the form of a subcutaneous implant the compound is suspended or dissolved in a slowly dispersed material known to those skilled in the art, or administered in a device which slowly releases the active material through the use of a constant driving force such as an osmotic pump. In such cases constant administration over periods ranging from 20 to 120 days are possible with the active ingredient being released at from 0.1 to 10 mg/kg/day.

Because the hIGF-I analogs act synergistically with platelet-derived growth factor (PDGF) or other competence factors such as fibroblast growth factor (FGF) to stimulate DNA synthesis and cell replication in human fibroblasts, such analogs are useful to promote would healing especially in cases where endogenous hIGF levels are low. Thus, the instant IGF-I analogs may be administered in combination with PDGF or FGF. The compounds could be administered parenterally, either subcutaneously, intramuscularly or intravenously using pharmaceutically acceptable parenteral formulation ingredients such as those listed above. The compounds would be administered at a dose of from 0.1 to 100 mg/kg, preferably from 1 to 10 mg/kg. Preferably, however, the compounds are administered topically when used as an agent to promote wound healing. Typical formulations for topical application are liquid, paste, ointment and spray formulations. The formulations could also be incorporated into a dressing which would be applied to the wound. The dressing would slowly release the compound directly to the site needing treatment.

The compounds would be incorporated into the topical formulation at concentrations of from 0.003 to 10% by weight with most formulations requiring from 0.3 to 3%. The concentration could be adjusted to provide for daily doses of from 0.06 to 2 mg of the active compound with allowance made to provide for multiple applications during any particular day.

The instant compounds may also be useful as erythropoietic agents possibly by virtue of their ability to stimulate late erythroid precursor differentiation. In such cases the compounds are administered parenterally as described above. The compounds may be administered either alone or in combination with erythropoietin to promote the production of red blood cells. For such uses the compounds are administered at doses of from 0.1 to 100 mg/kg, preferably from 1 to 10 mg/kg. Such doses are on a daily basis and if needed, the dose may be divided into multiple daily doses. Attached hereto are figures which further describe and explain the instant invention.

FIG. 1 describes the preparation of the recombinant plasmid pα2IGF132 from plasmid pα2 and plasmid phIGF by selective cleavage and recombination. The plasmid encodes for the 71-amino acid analog of human IGF-I.

FIG. 2 describes a replacement gene fragment for the NdeI/BstEII position of plasmid pJY1. The replacement fragment was in turn formed by the ligation of four oligonucleotides IGF132, IGF133, IGF134 and IGF135.

FIG. 3A describes the DNA gene sequence and the analog it encodes which is inserted by ligation into plasmid pα2IGF132.

FIGS. 3B, 3C and 3D similarly describe the DNA gene sequence and analogs for IGF122, IGF130 and IGF252 respectively.

Figure 4:
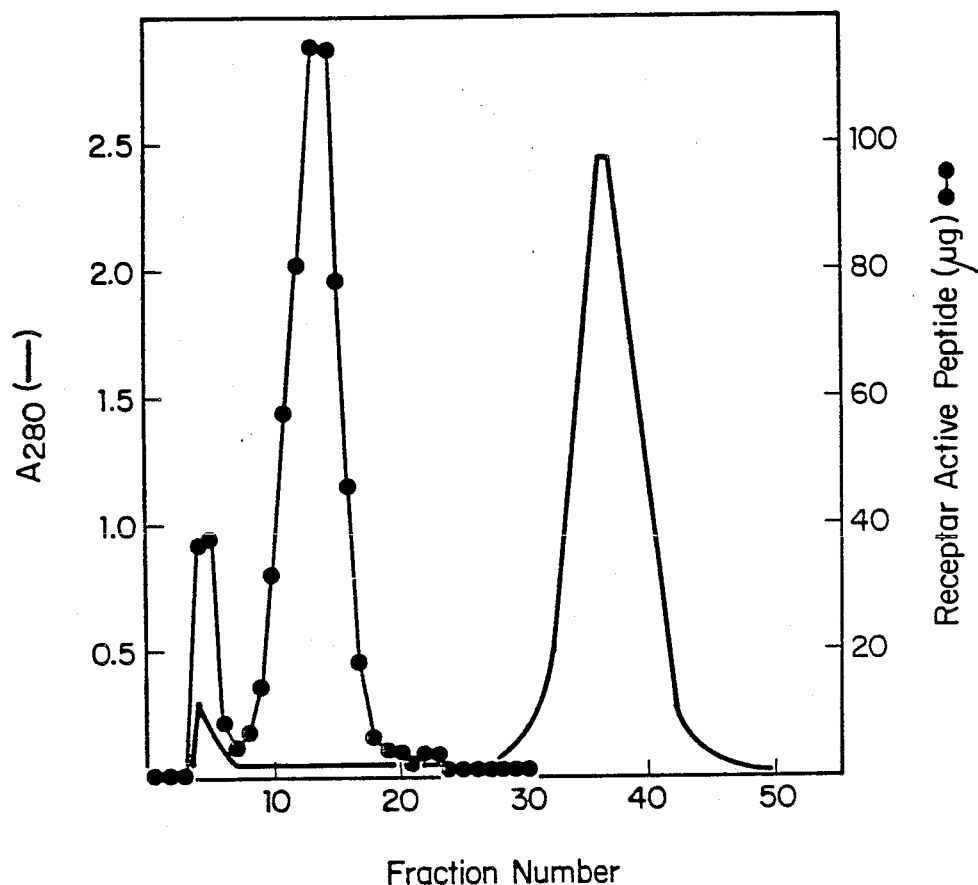

FIG. 4 describes the elution profile of analog IGF132 in a Biogel P10 gel filtration column.

Figure 5:
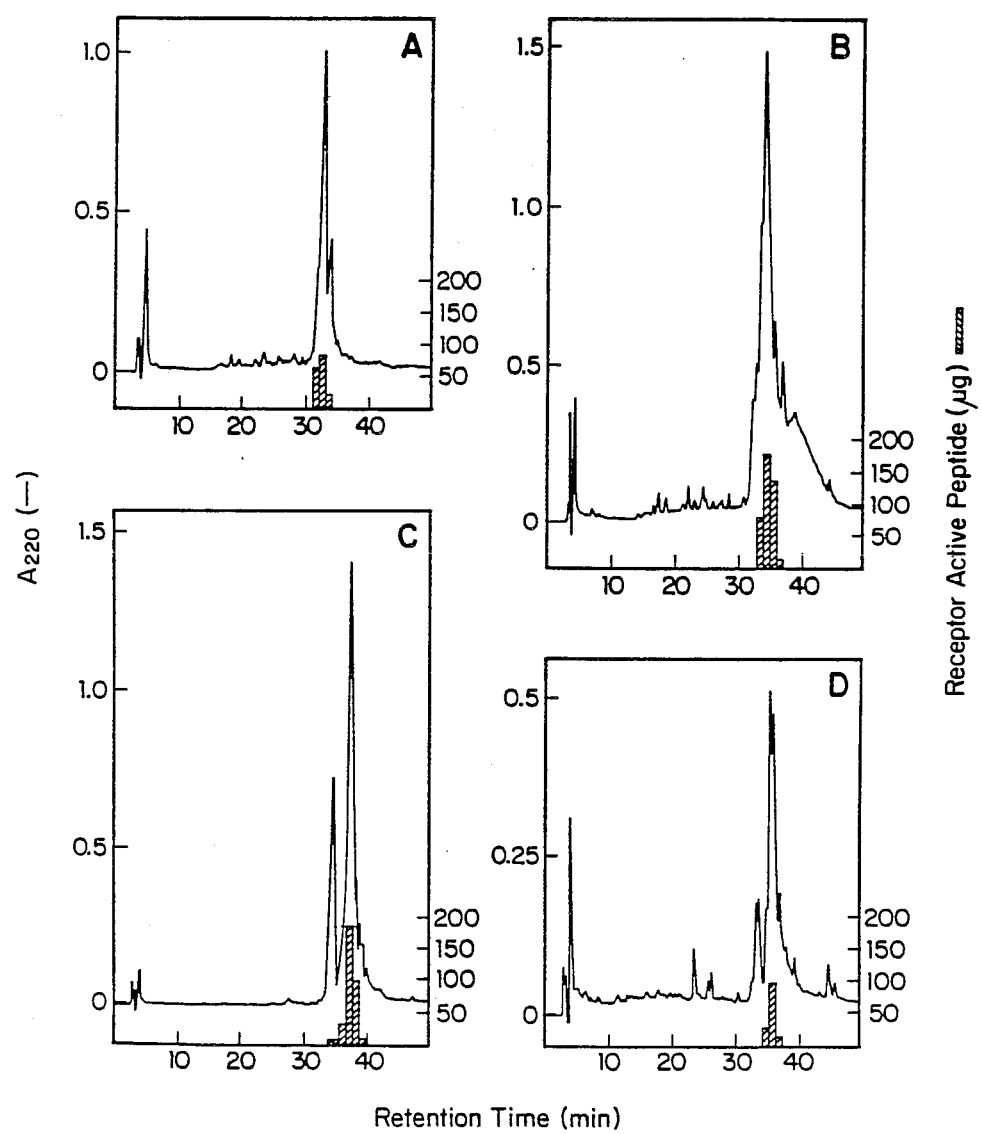

FIG. 5 describes the purification of the Biogel P10 active peaks from the preparation of A (IGF132), B (IGF122), C (IGF130) and D (IGF252) by high pressure liquid chromatography.

FIG. 6 describes the binding of analogs A (IGF132) B (IGF122), C (IGF130) and D (IGF252) to type I IGF receptors in comparison to wild type recombinant hIGF-I. In the figure, analog A is represented by "O", B by "◊", C by "♦" and D by "▲", and wild type IGF-I by "●".

FIG. 7 describes the binding of analog A (IGF132) B (IGF122), C (IGF130) and D (IGF252) to human serum carrier proteins in comparison to the binding of wild type hIGF-I. The hIGF-I is tightly bound to serum carrier proteins while analogs IGF132 and IGF252 are very weakly bound. The same representations shown in FIG. 6 are employed in this figure.

FIG. 8 describes the binding of Analog A (IGF132) and hIGF-I to native binding protein in rat serum. The h-IGF-I binds in a saturable fashion whereas binding of analog A (IGF132) is not observed.

FIG. 9 describes a comparison of biological activities of IGF-I with analogs A (IGF132) and D (IGF252) in the ability to stimulate DNA synthesis in 3T3 cells. Analogs A and D are observed to be 10 times more potent than wild-type IGF-I.

Figure 10:
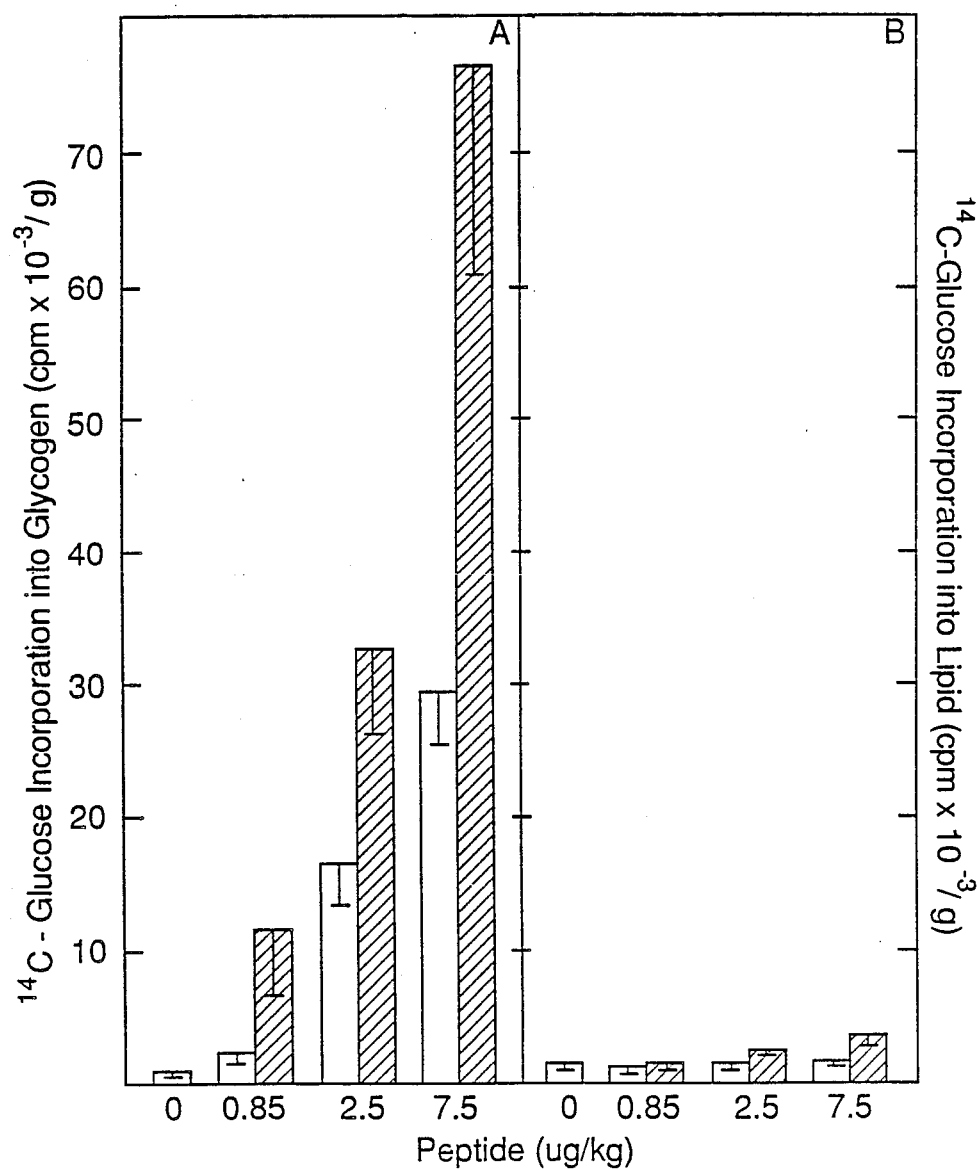

FIG. 10 describes a comparison of the ability of IGF-I and IGF252 to stimulate glycogen synthesis in rat diaphragm (part A) or lipid synthesis in rat adipose tissue (part B) in vivo. IGF252 is at least 2 fold more potent than IGF-I in stimulating glycogen synthesis in vivo. Neither IGF-I nor IGF252 stimulate lipid synthesis at these doses.

EXAMPLE

Construction of the IGF132 Analog Gene

A synthetic gene encoding the 70 amino acids of hIGF-I has been assembled and cloned into pBR322 to yield plasmid phIGF. Plasmid phIGF was modified to form plasmid pJY1 as described in FIG. 1. Four oligonucleotides: IGF132-5' TATG CCGC ATC CTT TCC TTG GAT AAA AGA TTT GTA AAC CAA CAT 3'; IGF133-5' ACA CAA ATG TTG GTT TAC AAA TCT TTT ATC CAA GGA AAG GAT CCG GCA 3'; IGF134-5' TTG TGT GGC TCC CAT CTG GTT GAA GCT TTG TAC TTG GTT TGC G 3'; and IGF135-5' GTC ACC GCA AAC CAA GTA CAA AGC TTC AAC GAG ATG GGA GCC 3' were ligated to form a NdeI/BstEII replacement fragment (FIG. 2). This fragment was inserted into pJY1 digested with endonuclease NdeI and BstEII. Transformation of E. coli with the ligation mixture yields bacteria carrying the plasmid pJY132. The DNA sequence and the analog IGF it encodes is shown in FIG. 3A.

Expression of Analog IGF132

The Bam HI IGF132 gene cassette from plasmid pJY132 was ligated into Bam HI digested pα2 as indicated in FIG. 1. The plasmid with the IGF132 cassette in pα2 in the proper orientation was designated pα-2IGF132. This plasmid was introduced into the yeast strain BJ1995. Yeast strain carrying the pα2IGF132 plasmid secrete the protein IGF132 into the growth media.

Expression and Purification of Mutant hIGF I Peptides

Saccharomyces cerevisiae strain BJ1995 (MAT α, leu2, trpl, ura3, prbl-1122, pep4-3, cir) was transformed with the appropriate expression plasmid and transformants were selected on leucine minus plates. Cells were grown to saturation in 1 liter of 5x leu(-) media, pH 4.8, containing 0.85% yeast nitrogen base without amino acids and ammonium sulfate supplemented with 4% glucose, 1% ammonium sulfate, 0.6% sodium hydroxide, 0.03% L-isoleucine, 0.03% L-phenylalanine, 0.025% L-tyrosine, 0.02% L-lysine, 0.02% L-tryptophan, 0.02% uracil, 0.02% adenine, 0.01% L-arginine, 0.005% methionine, 0.005% L-histidine, 29 μM ferric chloride, 25 μM zinc sulfate, and 1% succinic acid. Cells were removed by centrifugation at 3000 x g. The cleared supernatant was mixed with 10 g of BioRex 70 equilibrated in 1% succinic acid, pH 4.8. After stirring for 3 hours at 4° C., the resin was poured into a 2.5 cm column and washed with 1L of 1% succinic acid, pH 4.8. The peptide was eluted with 1M ammonium acetate, pH 8. Receptor active material was pooled, concentrated to 4 ml, then applied to a 2.5×90 cm Biogel P10 (200-400 mesh) column equilibrated in 1N acetic acid. Gel filtration was carried out at 30 ml per hour. Twelve ml fractions were collected and assayed for IGF-like activity by the radioreceptor assay. Active fractions were pooled and lyophilized. The activity was reconstituted in 0.2 ml 0.05% trifluoroacetic acid, 15% acetonitrile and loaded onto a C18 μBondapak (0.46×25 cm, 10 micron, Waters) reverse phase HPLC column. The peptides were eluted from the column using a 15-50% acetonitrile gradient in 0.05% trifluoroacetic acid. The flow rate was 1 ml per minute and 1 minute fractions were collected and assayed by receptor assay. Active fractions were pooled and lyophilized.

The purified peptide was quantitated by amino acid analysis and stored at −20° C. in 0.1 N acetic acid at a concentration of 0.1 mM.

Characterization of IGF Analogs

Quantitative amino acid analysis was employed to determine the concentration of purified analogs. The amino acid composition is consistent with that expected for the analogs.

Binding of the analogs to type I IGF receptor is shown in FIG. 6. Analog A (IGF132), B (IGF122), C (IGF130) and D (IGF252) inhibit the binding of $^{125}$I-hIGF-I to human placental membranes with a IC$_{50}$ of 12 nM, 4.5 nM, 5.3 nM, and 5.0 nM respectively, compared to 5.6 nM for wild type recombinant hIGF-I. Binding of analog 132 to human serum carrier proteins is shown in FIG. 7. Recombinant wild type hIGF-I inhibits binding of $^{125}$I-hIGF-I to acid stable human carrier proteins with a IC$_{50}$ of 0.42 nM, analog IGF132 showed little ability to inhibit this binding with a IC$_{50}$>1000 nM. IGF130, IGF122 and IGF252 inhibit binding with IC$_{50}$ values of 1.8 nM, 2.1 nM and 300 nM respectively.

$^{125}$I-labelled analog IGF132 was monitored for the ability to bind components in normal rat serum. When $^{125}$I-IGF or $^{125}$I-IGF132 is chromatographed without prior incubation with serum, the radioactivity is eluted in a broad peak which migrates at the position expected for a 7.5 kD peptide (FIG. 8A). After incubation of $^{125}$I-IGF with rat serum, a radioactive peak appears which elutes at the position expected for a 150 kD protein, and the amount of radioactivity in the free $^{125}$I-αIGF peak decreases (FIG. 8B (●)). The $^{125}$I-αIGF bound to the 150 kD species represents 36%±5% of the total $^{125}$I-IGF-I in the incubation. When the incubation is performed in the presence of 1 μg unlabelled IGF, only one radioactive peak is observed and this corresponds to unbound $^{125}$I-IGF (FIG. 8B (0)). Thus, under the conditions of this assay, the binding of $^{125}$I-IGF to the 150 kD species from rat serum is saturable.

After incubation of $^{125}$I-IGF132 with rat serum, only free radioactive peptide is eluted (FIG. 8C (●)). The presence of 1 μg unlabelled IGF132 in the incubation does not significantly change the radioactive profile (FIG. 8C (0)).

IGF-I stimulates DNA synthesis in mouse 3T3 cells. As shown in FIG. 9, IGF252 and IGF132 stimulate DNA synthesis in these cells with about 10-fold higher potency then wild type IGF-I.

IGF-I stimulates the incorporation of $^{14}$C-glucose into glycogen in the rat diaphragm in vivo. This process is mediated by the type 1 IGF receptor. As shown in FIG. 10, part A, IGF252 is at least two fold more potent than wild type IGF-I. As expected, neither IGF-I nor IGF252 stimulates the incorporation of $^{14}$C-glucose into lipid in adipose tissue. Adipose tissue does not have type 1 IGF receptors.

What is claimed is:

1. A synthetic polypeptide analog of hIGF-I which has the structure:

A$_1$-A$_2$-A$_3$-A$_4$-LCG-A$_5$-A$_6$-LV-A$_7$AL-A$_8$-A$_9$-R$_1$ wherein:
A$_1$ is G, V, or FV;
A$_2$ is P or N;
A$_3$ is E or Q;
A$_4$ is T, H or A;
A$_5$ is A or S;
A$_6$ is E or H;
A$_7$ is D or E;
A$_8$ is Q or Y;
A$_9$ is F or L; and
R$_1$ is VCGDRGFYFNKPTGYGSSSRRAPQT-GIVDECCFRSCDLRRLEMYCAPLKPAKSA
provided that the A$_1$ to A$_9$ groups and R$_1$ do not constitute GPETLCGAELVDALQF-R$_1$.

2. The peptide of claim 1 wherein:
A$_1$ is G, V, or FV;
A$_2$ is P or N;
A$_3$ is Q;
A$_4$ is A;
A$_5$ is A or S;
A$_6$ is E or H;
A$_7$ is D or E;
A$_8$ is Y; and
A$_9$ is L.

3. The peptide of claim 1 which is: FVNQHLCGSHLVEALYL-R$_1$.

4. The peptide of claim 1 which is: GPETLCGA-ELVDALYL-R$_1$.

5. The peptide of claim 1 which is: GPQALCGA-ELVDALQF-R$_1$.

6. The peptide of claim 1 which is: GPQALCGA-ELVDALYL-R$_1$.

7. The peptide of claim 1 which is: VNQHLCGSHLVEALYL-R$_1$.

8. A composition useful for the promotion of lactation, growth and feed efficiency, woulnd healing or stimulating erythropoiesis in animals, or increasing the lean and decreasing the fat content of meat producing animals which comprises an inert carrier and an effective amount of a synthetic polypeptide analog of hIGF-I of claim 1.

9. A method for the promotion of lactation in animals which comprises administering to a lactating animal a synthetic polypeptide analog of hIGF-I of claim 1.

10. A method for promoting growth and feed efficiency in animals which comprises administering to such animals a synthetic polypeptide analog of hIGF-I of claim 1.

11. A method for increasing the lean and decreasing the fat content of meat producing animals which comprises administering to such animals a synthetic polypeptide analog of hIGF-I of claim 1.

12. A method for promoting wound healing in animals which comprises administering to a wounded animal a synthetic polypeptide analog of hIGF-I of claim 1.

13. A method for stimulating erythropoiesis in animals which comprises administering to an animal in need of erythropoiesis a synthetic polypeptide analog of hIGF-I of claim 1.

* * * * *